US012723103B2

(12) United States Patent
Venter et al.

(10) Patent No.: US 12,723,103 B2
(45) Date of Patent: Sep. 1, 2026

(54) HOT-START ANTIBODIES FOR TAQ DNA POLYMERASE VARIANT

(71) Applicant: Watchmaker Genomics, Inc., Boulder, CO (US)

(72) Inventors: Phillip Venter, Cape Town (ZA); Bjarne Faurholm, Cape Town (ZA); Eric van der Walt, Cape Town (ZA)

(73) Assignee: Watchmaker Genomics, Inc., Boulder, CO (US)

( * ) Notice: Subject to any disclaimer, the term of this patent is extended or adjusted under 35 U.S.C. 154(b) by 0 days.

(21) Appl. No.: 19/294,142

(22) Filed: Aug. 7, 2025

(65) Prior Publication Data

US 2026/0042864 A1 Feb. 12, 2026

Related U.S. Application Data

(60) Provisional application No. 63/681,443, filed on Aug. 9, 2024.

(51) Int. Cl.

| | |
|---|---|
| ***C07K 16/00*** | (2006.01) |
| ***C07K 16/40*** | (2006.01) |
| ***C12Q 1/6804*** | (2018.01) |
| *C12Q 1/686* | (2018.01) |

(52) U.S. Cl.
CPC ............ *C07K 16/40* (2013.01); *C12Q 1/6804* (2013.01); *C12Y 207/07007* (2013.01); *C07K 2317/76* (2013.01); *C12Q 1/686* (2013.01)

(58) Field of Classification Search
None
See application file for complete search history.

(56) References Cited

U.S. PATENT DOCUMENTS

| | | | |
|---|---|---|---|
| 5,338,671 | A | 8/1994 | Scalice et al. |
| 2016/0369011 | A1 | 12/2016 | Grasso et al. |
| 2022/0135665 | A1 | 5/2022 | Xie et al. |

OTHER PUBLICATIONS

International Search Report and Written Opinion for Application No. PCT/US2025/041230, mailed Oct. 22, 2025.

*Primary Examiner* — Mark Halvorson
(74) *Attorney, Agent, or Firm* — Wolf, Greenfield & Sacks, P.C.

(57) ABSTRACT

This disclosure relates to Taq polymerase binding antibody compositions and methods of use for nucleic acid amplification.

18 Claims, 2 Drawing Sheets

Specification includes a Sequence Listing.

HOT-START ANTIBODIES FOR TAQ DNA POLYMERASE VARIANT

RELATED APPLICATIONS

This application claims the benefit under 35 U.S.C. § 119(e) of U.S. Provisional Application No. 63/681,443, filed Aug. 9, 2024, the entire contents of which are incorporated herein by reference.

REFERENCE TO AN ELECTRONIC SEQUENCE LISTING

The contents of the electronic sequence listing (W109470020US01-SEQ-ACZ.xml; Size: 16,245 bytes; and Date of Creation: Aug. 4, 2025) are herein incorporated by reference in its entirety.

BACKGROUND

The sensitivity and specificity of nucleic acid amplification techniques, such as polymerase chain reaction (PCR), often suffer from the presence of non-specific products and the formation of primer dimers. This can be caused by several factors, including annealing temperature, primer concentration, and polymerase activity during the setup of the reaction.

SUMMARY

Antibodies that can bind to Taq polymerase and inhibit its activity at low temperatures may be useful for preventing non-specific nucleic acid amplification. There is a need for antibody compositions that can inhibit Taq polymerase activity at reaction set-up temperatures, while allowing efficient polymerase activation during reaction temperatures to improve the sensitivity and specificity of amplification assays.

Provided herein are antibodies that can enhance the yield and/or homogeneity of primer extension products made by Taq polymerases. Antibodies of the disclosure may inhibit Taq polymerase activity at reaction set-up temperatures, reducing the likelihood of spurious amplification events such as primer-dimer formation or amplification of non-specific DNA sequences. Also provided herein are methods of amplifying a nucleic acid template using antibodies described herein.

Accordingly, in some aspects, the present disclosure provides an antibody that binds to a Taq polymerase, wherein the antibody comprises: (i) a heavy chain comprising a heavy chain variable region (VH); and (ii) a light chain comprising a light chain variable region (VL); wherein the VH comprises a heavy chain complementarity determining region 1 (CDR-H1) comprising an amino acid sequence as set forth in SEQ ID NO: 3, a heavy chain complementarity determining region 2 (CDR-H2) comprising an amino acid sequence as set forth in SEQ ID NO: 4, and a heavy chain complementarity determining region 3 (CDR-H3) comprising an amino acid sequence as set forth in SEQ ID NO: 5; and wherein the VL comprises a light chain complementarity determining region 1 (CDR-L1) comprising an amino acid sequence as set forth in SEQ ID NO: 6, a light chain complementarity determining region 2 (CDR-L2) comprising an amino acid sequence as set forth in SEQ ID NO: 7, and a light chain complementarity determining region 3 (CDR-L3) comprising an amino acid sequence as set forth in SEQ ID NO: 8.

In some embodiments, the VH comprises an amino acid sequence as set forth in SEQ ID NO: 9, and the VL comprises an amino acid sequence as set forth in SEQ ID NO: 10. In some embodiments, the heavy chain further comprises a heavy chain constant region (CH). In some embodiments, the light chain further comprises a light chain constant region (CL). In some embodiments, the heavy chain comprises an amino acid sequence as set forth in SEQ ID NO: 1, and the light chain comprises an amino acid sequence as set forth in SEQ ID NO: 2.

In some embodiments, the antibody is a full-length IgG, a Fab fragment, a F(ab') fragment, a $F(ab')^2$ fragment, or an Fv. In some embodiments, the antibody is a full-length rabbit IgG.

In some embodiments, the present disclosure provides a nucleic acid sequence encoding an antibody provided herein. In some embodiments, the present disclosure provides an expression vector comprising a nucleic acid sequence provided herein. In some embodiments, the present disclosure provides a cell comprising a nucleic acid sequence provided herein or an expression vector provided herein. In some embodiments, the cell is a mammalian cell. In some embodiments, the mammalian cell is a Chinese hamster ovary cell (CHO). In some embodiments, the cell is a bacterial cell.

In some embodiments, the present disclosure provides an antibody-polymerase complex, wherein the complex comprises: an antibody of the present disclosure; and a Taq polymerase. In some embodiments, the Taq polymerase is a wild-type Taq polymerase. In some embodiments, the Taq polymerase is a variant Taq polymerase. In some embodiments, activity of the Taq polymerase is inhibited when bound to the antibody. In some embodiments, the antibody-polymerase complex dissociates at a temperature greater than 80° C.

In some embodiments, the present disclosure provides a method of amplifying a nucleic acid template, the method comprising: combining, in a solution for amplifying the nucleic acid template: (a) an antibody of the present disclosure and a Taq polymerase, or an antibody-polymerase complex of the present disclosure; (b) a dNTP mixture; (c) a target nucleic acid template; and (d) an oligonucleotide primer comprising a polynucleotide that is complementary to the nucleic acid template. In some embodiments, the Taq polymerase is a wild-type Taq polymerase. In some embodiments, the Taq polymerase is a variant Taq polymerase.

In some embodiments, combining occurs at a first temperature. In some embodiments, the first temperature is below 30° C. In some embodiments, the antibody-polymerase complex remains intact at the first temperature. In some embodiments, the method further comprises bringing the solution to a denaturation temperature. In some embodiments, the antibody-polymerase complex dissociates at the denaturation temperature. In some embodiments, the denaturation temperature is at least 80° C. In some embodiments, the method further comprises bringing the solution to an annealing temperature. In some embodiments, the target nucleic acid template and the oligonucleotide primer anneal at the annealing temperature. In some embodiments, the method further comprises bringing the solution to an extension temperature. In some embodiments, the oligonucleotide primer is extended at the extension temperature.

In some embodiments, the method comprises, in consecutive order: (a) bringing the solution to the first temperature for a first predetermined amount of time; (b) bringing the solution to the denaturation temperature for a second predetermined amount of time; (c) bringing the solution to the denaturation temperature for a third predetermined amount of time; (d) bringing the solution to the annealing temperature for a fourth predetermined amount of time; and (e) bringing the solution to the extension temperature for a fifth predetermined amount of time.

In some embodiments, the method further comprises repeating a plurality of times: (a) bringing the solution to the denaturation temperature for the third predetermined amount of time; (b) bringing the solution to the annealing temperature for the fourth predetermined amount of time; and (c) bringing the solution to the extension temperature for the fifth predetermined amount of time. In some embodiments, the method further comprises bringing the solution to the extension temperature for a sixth predetermined amount of time.

In some embodiments, amplification of the nucleic acid template produces a plurality of amplicons. In some embodiments, amplification is carried out by PCR, qPCR, digital PCR, droplet digital PCR, linear amplification, or multiplex PCR.

In some embodiments, the present disclosure provides a kit comprising: (a) an antibody of the present disclosure; (b) a dNTP mixture; (c) a reaction buffer; and (d) a Taq polymerase. In some embodiments, the antibody, the dNTP mixture, the reaction buffer, and the Taq polymerase are provided as a single solution. In some embodiments, the Taq polymerase is a wild-type Taq polymerase. In some embodiments, the Taq polymerase is a variant Taq polymerase.

In some embodiments, the present disclosure provides a kit comprising: (a) an antibody-polymerase complex of the present disclosure; (b) a dNTP mixture; and (c) a reaction buffer. In some embodiments, the antibody-polymerase complex, the dNTP mixture, and the reaction buffer are provided as a single solution.

BRIEF DESCRIPTION OF THE DRAWINGS

The accompanying drawings are not intended to be drawn to scale. The drawings are illustrative only and are not required for enablement of the disclosure. For purposes of clarity, not every component may be labeled in every drawing. In the drawings.

DETAILED DESCRIPTION

Antibodies

Figure 1:
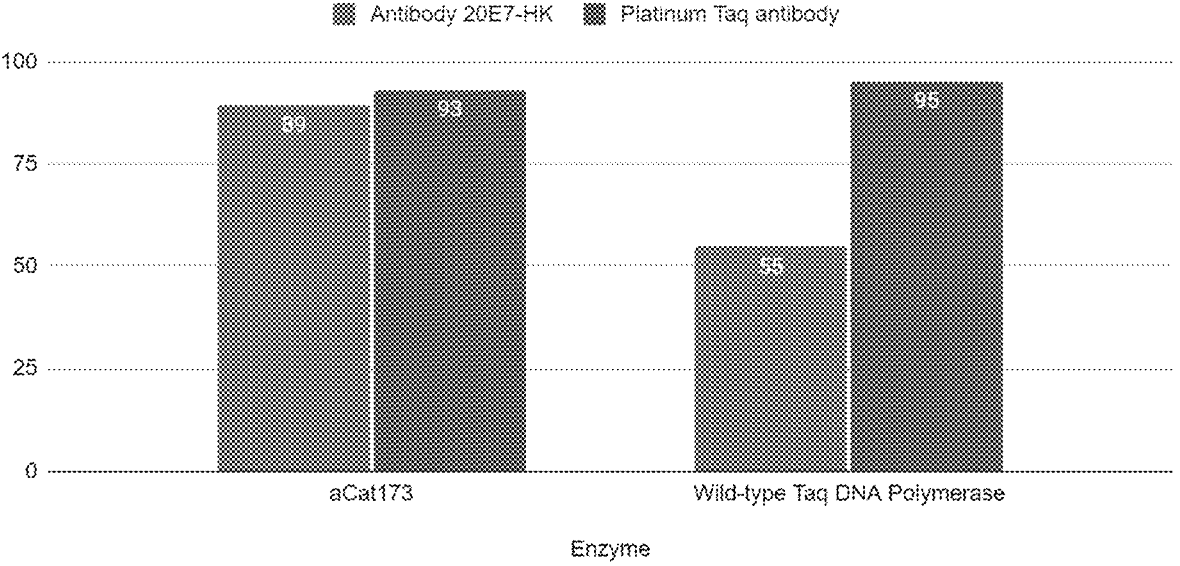
FIG. 1 shows percentage inhibition of a variant Taq DNA polymerase (aCat173) and a wild-type Taq DNA polymerase by antibody 20E7-HK and Platinum® Taq antibody at a 1:4 molar ratio (antibody:Taq DNA polymerase).

This disclosure provides antibodies that bind to Taq polymerase. In some embodiments, an antibody that binds to Taq polymerase comprises a heavy chain comprising a heavy chain variable region (VH) and a light chain comprising a light chain variable region (VL). In some embodiments, the VH comprises a heavy chain complementarity determining region 1 (CDR-H1) comprising an amino acid sequence as set forth in SEQ ID NO: 3, a heavy chain complementarity determining region 2 (CDR-H2) comprising an amino acid sequence as set forth in SEQ ID NO: 4, and a heavy chain complementarity determining region 3 (CDR-H3) comprising an amino acid sequence as set forth in SEQ ID NO: 5. In some embodiments, the VL comprises a light chain complementarity determining region 1 (CDR-L1) comprising an amino acid sequence as set forth in SEQ ID NO: 6, a light chain complementarity determining region 2 (CDR-L2) comprising an amino acid sequence as set forth in SEQ ID NO: 7, and a light chain complementarity determining region 3 (CDR-L3) comprising an amino acid sequence as set forth in SEQ ID NO: 8. In some embodiments, the VH comprises an amino acid sequence as set forth in SEQ ID NO: 9, and the VL comprises an amino acid sequence as set forth in SEQ ID NO: 10. In some embodiments, the heavy chain further comprises a heavy chain constant region (CH). In some embodiments, the light chain further comprises a light chain constant region (CL). In some embodiments, the heavy chain comprises an amino acid sequence as set forth in SEQ ID NO: 1. In some embodiments, the light chain comprises an amino acid sequence as set forth in SEQ ID NO: 2. Sequences of this disclosure are provided in Table 1.

TABLE 1

Sequences

| SEQ ID NO | Description | Sequence (5'-3') |
|---|---|---|
| 1 | 20E7-HK Heavy Chain | MGWSCIILFLVATATGVHSQSVEESGGRLVTPGTPLTLTCTASGFSLSNYEMNW VRQAPGKGLEWIGIIYGGSANIWYASWVKGRVTISKTSTTVDLKITSPTTEDTAT YFCARGVYVIYGGDDGSSRLDLWGQGTLVTVSSGQPKAPSVFPLAPCCGDTPSS TVTLGCLVKGYLPEPVTVTWNSGTLTNGVRTFPSVRQSSGLYSLSSVVSVTSSSQ PVTCNVAHPATNTKVDKTVAPSTCSKPTCPPPELLGGPSVFIFPPKPKDTLMISRT PEVTCVVVDVSQDDPEVQFTWYINNEQVRTARPPLREQQFNSTIRVVSTLPIAHQ DWLRGKEFKCKVHNKALPAPIEKTISKARGQPLEPKVYTMGPPREELSSRSVSLT CMINGFYPSDISVEWEKNGKAEDNYKTTPAVLDSDGSYFLYSKLSVPTSEWQRG DVFTCSVMHEALHNHYTQKSISRSPGK |
| 2 | 20E7-HK Light Chain | MGWSCIILFLVATATGVHSAAVLTQTPSPVSAAVGGTVTINCQSSQTVYNDNDL AWYQQKPGQPPKLLIYAASYLASGVPSRFSGSGFGTQFTLTISGVQCDDAATYY CLGGYDDATDNVFGGGTEVVVKGDPVAPTVLIFPPAADQVATGTVTIVCVANK YFPDVTVTWEVDGTTQTTGIENSKTPQNSADCTYNLSSTLTLTSTQYNSHKEYT CKVTQGTTSVVQSFNRGDC |
| 3 | 20E7-HK CDR-H1 | NYEMN |

TABLE 1-continued

| SEQ ID NO | Description | Sequence (5'-3') |
|---|---|---|
| 4 | 20E7-HK CDR-H2 | IIYGGSANIWYASWVKG |
| 5 | 20E7-HK CDR-H3 | GVYVIYGGDDGSSRLDL |
| 6 | 20E7-HK CDR-L1 | QSSQTVYNDNDLA |
| 7 | 20E7-HK CDR-L2 | AASYLAS |
| 8 | 20E7-HK CDR-L3 | LGGYDDATDNV |
| 9 | 20E7-HK VH | MGWSCIILFLVATATGVHSQSVEESGGRLVTPGTPLTLTCTASGFSLSNYEMNW VRQAPGKGLEWIGIIYGGSANIWYASWVKGRVTISKTSTTVDLKITSPTTEDTAT YFCARGVYVIYGGDDGSSRLDLWGQGTLVTVSS |
| 10 | 20E7-HK VL | MGWSCIILFLVATATGVHSAAVLTQTPSPVSAAVGGTVTINCQSSQTVYNDNDL AWYQQKPGQPPKLLIYAASYLASGVPSRFSGSGFGTQFTLTISGVQCDDAATYY CLGGYDDATDNVFGGGTEVVVK |
| 11 | Wild-type Taq DNA Polymerase | ATGAGGGGGATGCTGCCCCTCTTTGAGCCCAAGGGCCGGGTCCTCCTGGTGG ACGGCCACCACCTGGCCTACCGCACCTTCCACGCCCTGAAGGGCCTCACCAC CAGCCGGGGGGAGCCGGTGCAGGCGGTCTACGGCTTCGCCAAGAGCCTCCT CAAGGCCCTCAAGGAGGACGGGGACGCGGTGATCGTGGTCTTTGACGCCAA GGCCCCCTCCTTCCGCCACGAGGCCTACGGGGGGTACAAGGCGGGCCGGGC CCCCACGCCGGAGGACTTTCCCCGGCAACTCGCCCTCATCAAGGAGCTGGTG GACCTCCTGGGGCTGGCGCGCCTCGAGGTCCCGGGCTACGAGGCGGACGAC GTCCTGGCCAGCCTGGCCAAGAAGGCGGAAAAGGAGGGCTACGAGGTCCGC ATCCTCACCGCCGACAAAGACCTTTACCAGCTCCTTTCCGACCGCATCCACG CCCTCCACCCCGAGGGGTACCTCATCACCCCGGCCTGGCTTTGGGAAAAGTA CGGCCTGAGGCCCGACCAGTGGGCCGACTACCGGGCCCTGACCGGGGACGA GTCCGACAACCTTCCCGGGGTCAAGGGCATCGGGGAGAAGACGGCGAGGAA GCTTCTGGAGGAGTGGGGGAGCCTGGAAGCCCTCCTCAAGAACCTGGACCG GCTGAAGCCCGCCATCCGGGAGAAGATCCTGGCCCACATGGACGATCTGAA GCTCTCCTGGGACCTGGCCAAGGTGCGCACCGACCTGCCCCTGGAGGTGGAC TTCGCCAAAAGGCGGGAGCCCGACCGGGAGAGGCTTAGGGCCTTTCTGGAG AGGCTTGAGTTTGGCAGCCTCCTCCACGAGTTCGGCCTTCTGGAAAGCCCCA AGGCCCTGGAGGAGGCCCCCTGGCCCCCGCCGGAAGGGGCCTTCGTGGGCT TTGTGCTTTCCCGCAAGGAGCCCATGTGGGCCGATCTTCTGGCCCTGGCCGC CGCCAGGGGGGGCCGGGTCCACCGGGCCCCCGAGCCTTATAAAGCCCTCAG GGACCTGAAGGAGGCGCGGGGGCTTCTCGCCAAAGACCTGAGCGTTCTGGC CCTGAGGGAAGGCCTTGGCCTCCCGCCCGGCGACGACCCCATGCTCCTCGCC TACCTCCTGGACCCTTCCAACACCACCCCCGAGGGGGTGGCCCGGCGCTACG GCGGGGAGTGGACGGAGGAGGCGGGGGAGCGGGCCGCCCTTTCCGAGAGG CTCTTCGCCAACCTGTGGGGGAGGCTTGAGGGGGAGGAGAGGCTCCTTTGG CTTTACCGGGAGGTGGAGAGGCCCCTTTCCGCTGTCCTGGCCCACATGGAGG CCACGGGGGTGCGCCTGGACGTGGCCTATCTCAGGGCCTTGTCCCTGGAGGT GGCCGAGGAGATCGCCCGCCTCGAGGCCGAGGTCTTCCGCCTGGCCGGCCA CCCCTTCAACCTCAACTCCCGGGACCAGCTGGAAAGGGTCCTCTTTGACGAG CTAGGGCTTCCCGCCATCGGCAAGACGGAGAAGACCGGCAAGCGCTCCACC AGCGCCGCCGTCCTGGAGGCCCTCCGCGAGGCCCACCCCATCGTGGAGAAG ATCCTGCAGTACCGGGAGCTCACCAAGCTGAAGAGCACCTACATTGACCCCT TGCCGGACCTCATCCACCCCAGGACGGGCCGCCTCCACACCCGCTTCAACCA GACGGCCACGGCCACGGGCAGGCTAAGTAGCTCCGATCCCAACCTCCAGAA CATCCCCGTCCGCACCCCGCTTGGGCAGAGGATCCGCCGGGCCTTCATCGCC GAGGAGGGGTGGCTATTGGTGGCCCTGGACTATAGCCAGATAGAGCTCAGG GTGCTGGCCCACCTCTCCGGCGACGAGAACCTGATCCGGGTCTTCCAGGAGG GGCGGGACATCCACACGGAGACCGCCAGCTGGATGTTCGGCGTCCCCCGGG AGGCCGTGGACCCCCTGATGCGCCGGGCGGCCAAGACCATCAACTTCGGGG TCCTCTACGGCATGTCGGCCCACCGCCTCTCCCAGGAGCTAGCCATCCCTTA CGAGGAGGCCCAGGCCTTCATTGAGCGCTACTTTCAGAGCTTCCCCAAGGTG CGGGCCTGGATTGAGAAGACCCTGGAGGAGGGCAGGAGGCGGGGGTACGT GGAGACCCTCTTCGGCCGCCGCCGCTACGTGCCAGACCTAGAGGCCCGGGT GAAGAGCGTGCGGGAGGCGGCCGAGCGCATGGCCTTCAACATGCCCGTCCA GGGCACCGCCGCCGACCTCATGAAGCTGGCTATGGTGAAGCTCTTCCCCAGG CTGGAGGAAATGGGGGCCAGGATGCTCCTTCAGGTCCACGACGAGCTGGTC CTCGAGGCCCCAAAAGAGAGGGCGGAGGCCGTGGCCCGGCTGGCCAAGGA GGTCATGGAGGGGGTGTATCCCCTGGCCGTGCCCCTGGAGGTGGAGGTGGG GATAGGGGAGGACTGGCTCTCCGCCAAGGAGTGATACCACCCCATGCTGGC CCAAGCCAGCATGGGGGCCCCGGCAAAAGGTTTCTGGGGAAGTTACCAGGC ATGGTGGGCCGAAGGAAACAGGAAACAAGGGTATGAGGGTTTTTGCCCTA AAGAAAGGCCAGGGGGTCCTCCCGAAGGAAGGCTTCCAGGGGGATACCCCC |

TABLE 1-continued

| Sequences | | |
|---|---|---|
| SEQ ID NO | Description | Sequence (5'-3') |
| | | TGGGCCCAGGAGTAGCCCCTTTCCTCCAAAGGCCTGGGTGAAGGCTTTTAGC<br>CCTTTGGTCCTTTGGGAAGGGGCGCTTTTGACCTCCAAAGCCAGAAGGCGCC<br>TTCCCTTCTTCAAGACGAAGTCAACCTCCTGGTCCCTTTCCCGCCAGTAGTAC<br>ACCTCAAAGCCCCCGTGGGGGCCGTGGGCCAGAAGGTGGGCGCCCACGGCG<br>GTTTCCACGAGCCGCCCCATGAGGGCGGCGTCCGCCCACACCTCCTTTGGGG<br>AAAGCCCCAAGACCGCCGTGATGAGCCCCGTATTAAGGGCCAGGAGCTTGG<br>GGCTCGAGGCGCGGCGCCGGAAGGGCTCGGCGGCGTACTTCTGCAG |
| 12 | Wild-type Taq DNA Polymerase | MRGMLPLFEPKGRVLLVDGHHLAYRTFHALKGLTTSRGEPVQAVYGFAKSLLK<br>ALKEDGDAVIVVFDAKAPSFRHEAYGGYKAGRAPTPEDFPRQLALIKELVDLLG<br>LARLEVPGYEADDVLASLAKKAEKEGYEVRILTADKDLYQLLSDRIHALHPEGY<br>LITPAWLWEKYGLRPDQWADYRALTGDESDNLPGVKGIGEKTARKLLEEWGSL<br>EALLKNLDRLKPAIREKILAHMDDLKLSWDLAKVRTDLPLEVDFAKRREPDRER<br>LRAFLERLEFGSLLHEFGLLESPKALEEAPWPPPEGAFVGFVLSRKEPMWADLL<br>ALAAARGGRVHRAPEPYKALRDLKEARGLLAKDLSVLALREGLGLPPGDDPML<br>LAYLLDPSNTTPEGVARRYGGEWTEEAGERAALSERLFANLWGRLEGEERLLW<br>LYREVERPLSAVLAHMEATGVRLDVAYLRALSLEVAEEIARLEAEVFRLAGHPF<br>NLNSRDQLERVLFDELGLPAIGKTEKTGKRSTSAAVLEALREAHPIVEKILQYRE<br>LTKLKSTYIDPLPDLIHPRTGRLHTRFNQTATATGRLSSSDPNLQNIPVRTPLGQR<br>IRRAFIAEEGWLLVALDYSQIELRVLAHLSGDENLIRVFQEGRDIHTETASWMFG<br>VPREAVDPLMRRAAKTINFGVLYGMSAHRLSQELAIPYEEAQAFIERYFQSFPK<br>VRAWIEKTLEEGRRRGYVETLFGRRRYVPDLEARVKSVREAAERMAFNMPVQ<br>GTAADLMKLAMVKLFPRLEEMGARMLLQVHDELVLEAPKERAEAVARLAKEV<br>MEGVYPLAVPLEVEVGIGEDWLSAKE |

In some embodiments, the antibody is a full-length IgG, a Fab fragment, a F(ab') fragment, a $F(ab')^2$ fragment, or an Fv. In some embodiments, the antibody is a full-length rabbit IgG. In some embodiments, the antibody is a full-length cow IgG, a full-length goat IgG, a full-length chicken IgG, or a full-length mouse IgG. In some embodiments, the full-length IgG comprises a heavy chain constant region of isotype IgG1, IgG2, IgG3, or IgG4.

In some embodiments, a nucleic acid sequence encoding an antibody disclosed herein is provided. In some embodiments, the nucleic acid sequence encodes an amino acid comprising the VH of the antibody and an amino acid comprising the VL of the antibody. In some embodiments, the VH comprises a heavy chain complementarity determining region 1 (CDR-H1) comprising the amino acid sequence of SEQ ID NO: 3, a heavy chain complementarity determining region 2 (CDR-H2) comprising the amino acid sequence of SEQ ID NO: 4, and a heavy chain complementarity determining region 3 (CDR-H3) comprising the amino acid sequence of SEQ ID NO: 5. In some embodiments, the VL comprises a light chain complementarity determining region 1 (CDR-L1) comprising the amino acid sequence of SEQ ID NO: 6, a light chain complementarity determining region 2 (CDR-L2) comprising the amino acid sequence of SEQ ID NO: 7, and a light chain complementarity determining region 3 (CDR-L3) comprising an amino acid sequence as set forth in SEQ ID NO: 8. In some embodiments, the VH comprises an amino acid sequence as set forth in SEQ ID NO: 9, and the VL comprises an amino acid sequence as set forth in SEQ ID NO: 10. In some embodiments, the nucleic acid sequence encodes an amino acid comprising the heavy chain of the antibody and an amino acid comprising the light chain of the antibody. In some embodiments, the heavy chain of the antibody comprises an amino acid sequence as set forth in SEQ ID NO: 1, and the light chain of the antibody comprises an amino acid sequence as set forth in SEQ ID NO: 2.

Expression Vectors and Cells

In some embodiments, this disclosure provides an expression vector comprising a polynucleotide encoding an antibody described herein. An expression vector, or an expression construct, is a plasmid or other DNA molecule designed to facilitate the expression of a specific gene or protein in a cell. Expression vectors typically contain several key elements that enable gene expression, including: 1) a promoter, which is a DNA sequence that initiates transcription allowing the gene of interest to be transcribed into messenger RNA; 2) a gene of interest or insert, which is the DNA sequence that encodes a protein (e.g., an antibody) or RNA molecule to be produced; 3) a selectable marker, which is a gene that confers resistance to an antibiotic (e.g., ampicillin or kanamycin) or another selective agent; 4) an origin of replication, which is a sequence that allows the vector to replicate autonomously within a cell and ensures that the vector and its inserted gene are maintained as the host cells divide; and 5) a terminator sequence, which is a sequence downstream of the gene of interest that signals the end of transcription and ensures that the mRNA transcript is correctly processed.

In some embodiments, this disclosure provides a cell comprising an antibody described herein, a nucleic acid sequence described herein, or an expression vector described herein. In some embodiments, a cell comprises (e.g., has been transformed with) an expression vector comprising a nucleic acid that encodes an amino acid comprising the VH of the antibody and an amino acid comprising the VL of the antibody. In some embodiments, the VH comprises a heavy chain complementarity determining region 1 (CDR-H1) comprising the amino acid sequence of SEQ ID NO: 3, a heavy chain complementarity determining region 2 (CDR-H2) comprising the amino acid sequence of SEQ ID NO: 4, and a heavy chain complementarity determining region 3 (CDR-H3) comprising the amino acid sequence of SEQ ID NO: 5 In some embodiments, the VL comprises a light chain complementarity determining region 1 (CDR-L1) comprising the amino acid sequence of SEQ ID NO: 6, a light chain complementarity determining region 2 (CDR-L2) comprising the amino acid sequence of SEQ ID NO: 7, and a light chain complementarity determining region 3 (CDR-L3) comprising an amino acid sequence as set forth in SEQ ID NO: 8. In some embodiments, the VH comprises an amino acid sequence as set forth in SEQ ID NO: 9, and the VL comprises an amino acid sequence as set forth in SEQ ID NO: 10. In some embodiments, a cell comprises (e.g., has been transformed with) an expression vector comprising a nucleic acid that encodes an amino acid comprising the heavy chain of the antibody and an amino acid comprising the light chain of the antibody. In some embodiments, the heavy chain of the antibody comprises an amino acid sequence as set forth in SEQ ID NO: 1, and the light chain of the antibody comprises an amino acid sequence as set forth in SEQ ID NO: 2.

In some embodiments, the cell is a mammalian cell. In some embodiments, the mammalian cell is a Chinese Hamster Ovary cell (CHO). In some embodiments, the mammalian cell is a HEK293 cell, a NS0 cell, or an SP2/0 cell. In some embodiments, the cell is a bacterial cell. Non-limiting examples of bacterial cells include *Escherichia coli, Bacillus subtilis, Streptomyces* species, and *Pseudomonas putida*. In some embodiments, the cell is an insect cell (e.g., an Sf9 cell or an Sf21 cell). In some embodiments, the cell is a yeast cell (e.g., a *Saccharomyces cerevisiae* cell).

Polymerases

A polymerase includes an enzyme that catalyzes the polymerization of nucleotides to synthesize nucleic acid polymers. DNA polymerases are crucial components of nucleic acid amplification techniques, such as polymerase chain reaction (PCR). Taq polymerase is a DNA polymerase enzyme derived from the bacterium *Thermus aquaticus*. Wild-type Taq polymerase is a heat-resistant polymerase known for its thermal stability, with a half-life of 40 minutes at 90° C. Taq polymerase catalyzes the synthesis of a complementary DNA strand using a single-stranded DNA template and DNA primers, following the standard Watson-Crick base-pairing rules to synthesize the new DNA strand.

In some embodiments, the Taq polymerase is a wild-type Taq polymerase (e.g., SEQ ID NOs: 11 and 12). A wild-type Taq polymerase refers to the naturally-occurring form of the *Thermus aquaticus* Taq polymerase. In some embodiments, the Taq polymerase is a variant Taq polymerase. In some embodiments, the variant Taq polymerase is Watchmaker Genomics catalog number aCat173. A variant Taq polymerase is a Taq polymerase that comprises one or more (e.g., 1, 2, 3, 4, 5, 6, 7, 8, 9, 10, or more) modifications relative to a wild-type Taq polymerase. Variant Taq polymerases can be engineered to include the one or more modifications (e.g., amino acid substitutions, insertions, deletions, and/or post-translational modifications) through site-directed mutagenesis, random mutagenesis, gene synthesis, directed evolution, genome editing, and/or chemical modification. Relative to a wild-type Taq polymerase, a variant Taq polymerase may exhibit enhanced thermal stability and/or improved fidelity, processivity, and/or resistance to PCR inhibitors.

Antibody-Polymerase Complexes

In some embodiments, this disclosure provides an antibody-polymerase complex, wherein the complex comprises an antibody described herein and a Taq polymerase (e.g., a variant Taq polymerase). As used herein, the term "antibody-polymerase complex" refers to an antibody that is bound to a Taq polymerase.

In some embodiments, the complex comprises: 1) an antibody comprising a heavy chain comprising a heavy chain variable region (VH) and a light chain comprising a light chain variable region (VL), wherein the VH comprises a heavy chain complementarity determining region 1 (CDR-H1) comprising an amino acid sequence as set forth in SEQ ID NO: 3, a heavy chain complementarity determining region 2 (CDR-H2) comprising an amino acid sequence as set forth in SEQ ID NO: 4, a heavy chain complementarity determining region 3 (CDR-H3) comprising an amino acid sequence as set forth in SEQ ID NO: 5, and wherein the VL comprises a light chain complementarity determining region 1 (CDR-L1) comprising an amino acid sequence as set forth in SEQ ID NO: 6, a light chain complementarity determining region 2 (CDR-L2) comprising an amino acid sequence as set forth in SEQ ID NO: 7, and a light chain complementarity determining region 3 (CDR-L3) comprising an amino acid sequence as set forth in SEQ ID NO: 8; and 2) a Taq polymerase. In some embodiments, the complex comprises: 1) an antibody comprising a VH comprising an amino acid sequence as set forth in SEQ ID NO: 9, and a VL comprising an amino acid sequence as set forth in SEQ ID NO: 10; and 2) a Taq polymerase. In some embodiments, the complex comprises: 1) an antibody comprising a heavy chain and a light chain, wherein the heavy chain comprises an amino acid sequence as set forth in SEQ ID NO: 1 and the light chain comprises an amino acid sequence as set forth in SEQ ID NO: 2; and 2) a Taq polymerase. In some embodiments, the Taq polymerase is a wild-type Taq polymerase (e.g., SEQ ID NOs: 11 and 12). In some embodiments, the Taq polymerase is a variant Taq polymerase.

In some embodiments, an antibody of the present disclosure binds to Taq polymerase. As used herein, the term "an antibody that binds to Taq polymerase" refers to an antibody that is capable of binding Taq polymerase (e.g., wild-type Taq polymerase or variant Taq polymerase). In some embodiments, an antibody that binds to Taq polymerase binds to wild-type Taq polymerase with a high degree of selectivity and binding affinity relative to binding to an unrelated, non-Taq DNA polymerase. In some embodiments, an antibody that binds to Taq polymerase binds to variant Taq polymerase with a high degree of selectivity and binding affinity relative to binding to an unrelated, non-Taq DNA polymerase. In some embodiments, the extent of binding of an antibody of the present disclosure to an unrelated, non-Taq DNA polymerase is less than about 15%, less than about 10%, less than about 5%, or less than about 2.5% of the extent of binding of an antibody of the present disclosure to a Taq polymerase as measured, e.g., by an enzyme-linked immunosorbent assay (ELISA). In some embodiments, an antibody of the present disclosure does not detectably bind to an unrelated, non-Taq DNA polymerase as measured, e.g., by an enzyme-linked immunosorbent assay (ELISA).

In some embodiments, when an antibody of the present disclosure is bound to a Taq polymerase, the activity of the Taq polymerase is inhibited. In some embodiments, the inhibited Taq polymerase activity is polymerization. Polymerization can be assessed by a variety of methods including, but not limited to, malachite green-based assays and fluorometric-based assays (e.g., EvaEZ Fluorometric Polymerase Activity Assay Kit, Biotium, USA). Using these assays, the extent to which an antibody inhibits Taq polymerase activity can be evaluated by comparing the amplification signal obtained in the presence of a functional antibody to the amplification signal obtained in the presence of a heat-inactivated antibody. Such a measurement can be represented as a percentage inhibition, which is calculated using the following formula:

Percentage Inhibition (%) =

$$\left(1-\frac{\text{Signal with functional antibody}}{\text{Signal with heat}-\text{inactivated antibody}}\right)\times 100\%.$$

A higher percentage inhibition value indicates more effective inhibition of Taq polymerase activity. Percentage inhibition values of at least 80% (e.g., at least 80%, at least 85%, at least 90%, at least 95%, at least 96%, at least 97%, at least 98%, at least 99%, or 100%) indicates effective inhibition of a Taq polymerase.

The extent to which an antibody inhibits Taq polymerase activity varies with different molar ratios of polymerase to antibody. The theoretical minimum molar ratio of polymerase to antibody required to inhibit Taq polymerase is 1:0.5 for a bivalent antibody, which is capable of binding and inhibiting two polymerase molecules per antibody molecule. In some embodiments, an antibody of the present disclosure exhibits effective inhibition (e.g., having a percentage inhibition of at least 80%) when the molar ratio of polymerase to antibody is between 1:0.4 and 1:1.3 (e.g., 1:0.4, 1:0.5, 1:0.6, 1:0.7, 1:0.8, 1:0.9, 1:1, 1:1.1, 1:1.2, or 1:1.3).

In some embodiments, a disclosed antibody inhibits activity of a variant Taq polymerase (e.g., aCat173) by a greater amount than a wildtype Taq polymerase. In some embodiments, binding of a disclosed antibody to a wildtype Taq polymerase inhibits the activity of the wildtype Taq polymerase by no more than about 65%. In some embodiments, binding of a disclosed antibody to a wildtype Taq polymerase inhibits the activity of the wildtype Taq polymerase by no more than about 62%.

Methods of Use

This disclosure also provides methods of amplifying a nucleic acid. In some embodiments, the method comprises combining, in a solution for amplifying the nucleic acid template: (a) an antibody of the present disclosure and a Taq polymerase, or an antibody-polymerase complex of the present disclosure; (b) a dNTP mixture; (c) a target nucleic acid template; and (d) an oligonucleotide primer comprising a polynucleotide that is complementary to the nucleic acid template. In some embodiments, the Taq polymerase is a wild-type Taq polymerase. In some embodiments, the Taq polymerase is a variant Taq polymerase. In some embodiments, amplification of the nucleic acid template produces a plurality of amplicons. In some embodiments, amplification is carried out by polymerase chain reaction (PCR), qPCR (quantitative real-time PCR), droplet digital PCR, linear amplification, or multiplex PCR.

In some embodiments, combining occurs at a first temperature. As used herein, the term "combining" refers to placing two or more substances together. In some embodiments, the antibody and the Taq polymerase are combined at a first temperature. In some embodiments, the first temperature is less than 30° C. In some embodiments, the first temperature is about 20° C., about 21° C., about 22° C., about 23° C., about 24° C., or about 25° C. In some embodiments, the first temperature is between about 22° C. and about 25° C. In some embodiments, the antibody and the Taq polymerase are further incubated for a first predetermined amount of time. In some embodiments, the first predetermined amount of time is at least 5 minutes, at least 10 minutes, or at least 15 minutes. In some embodiments, an antibody-polymerase complex is formed after combining the antibody and the Taq polymerase at a first temperature (e.g., between about 22° C. and about 25° C.) and incubating at said first temperature for a predetermined amount of time (e.g., 10 minutes). In some embodiments, the antibody-polymerase complex remains intact at the first temperature.

In some embodiments, the method further comprises bringing the solution to a denaturation temperature. The denaturation temperature is the temperature at which most (e.g., at least 80%, at least 85%, at least 90%, at least 95%, at least 97.5%, at least 99%, or 100%) of the double-stranded DNA molecules in a sample separate into two single-stranded DNA molecules. In some embodiments, the denaturation temperature is about 80° C., about 85° C., about 90° C., or about 98° C. In some embodiments, the denaturation temperature is at least 80° C., at least 85° C., at least 90° C., at least 95° C., or at least 98° C. In some embodiments, the solution is held at a denaturation temperature (e.g., about 95° C.) for a second predetermined amount of time. In some embodiments, the second predetermined amount of time is at least 10 seconds, at least 15 seconds, at least 20 seconds, at least 25 seconds, at least 30 seconds, at least 35 seconds, at least 40 seconds, at least 45 seconds, at least 50 seconds, at least 55 seconds, or at least 60 seconds. In some embodiments, the solution is held at a denaturation temperature (e.g., about 95° C.) for a third predetermined amount of time. In some embodiments, the third predetermined amount of time is at least 10 seconds, at least 15 seconds, at least 20 seconds, at least 25 seconds, at least 30 seconds, at least 35 seconds, at least 40 seconds, at least 45 seconds, at least 50 seconds, at least 55 seconds, or at least 60 seconds. In some embodiments, the antibody polymerase complex dissociates at the denaturation temperature (e.g., about 95° C.) after incubation at said denaturation temperature (e.g., about 95° C.) for a second predetermined amount of time (e.g., 60 seconds).

In some embodiments, the method further comprises bringing the solution to an annealing temperature. The annealing temperature is the temperature at which an oligonucleotide primer comprising a polynucleotide that is complementary to the nucleic acid template binds to the complementary sequences on the target nucleic acid template. In some embodiments, the target nucleic acid template and the oligonucleotide primer anneal at the annealing temperature. In some embodiments, the annealing temperature is about 55° C., about 60° C., about 65° C., about 70° C., or about 72° C. In some embodiments, the solution is held at an annealing temperature (e.g., about 60° C.) for a fourth predetermined amount of time. In some embodiments, the fourth predetermined amount of time is at least 10 seconds, at least 15 seconds, at least 20 seconds, at least 25 seconds, at least 30 seconds, at least 35 seconds, at least 40 seconds, at least 45 seconds, at least 50 seconds, at least 55 seconds, or at least 60 seconds.

In some embodiments, the method further comprises bringing the solution to an extension temperature. The extension temperature is the temperature at which the DNA polymerase enzyme synthesizes new DNA strands by adding complementary nucleotides to the template strand. In some embodiments, the oligonucleotide primer is extended at the extension temperature. In some embodiments, the extension temperature is about 68° C., about 70° C., or about 72° C. In some embodiments, the solution is held at an extension temperature (e.g., about 72° C.) for a fifth predetermined amount of time. In some embodiments, the fifth predetermined amount of time is at least 10 seconds, at least 15 seconds, at least 20 seconds, at least 25 seconds, at least 30 seconds, at least 35 seconds, at least 40 seconds, at least 45 seconds, at least 50 seconds, at least 55 seconds, or at least 60 seconds. In some embodiments, the solution is held at an extension temperature (e.g., about 72° C.) for a sixth predetermined amount of time. In some embodiments, the sixth predetermined amount of time is at least 10 seconds, at least 15 seconds, at least 20 seconds, at least 25 seconds, at least 30 seconds, at least 35 seconds, at least 40 seconds, at least 45 seconds, at least 50 seconds, at least 55 seconds, or at least 60 seconds.

In some embodiments, the method comprises, in consecutive order: (1) bringing the solution to a first temperature (e.g., between about 22° C. and about 25° C.) for a first predetermined amount of time (e.g., 10 minutes), which results in the formation of an antibody-polymerase complex (where an antibody and a Taq polymerase are provided separately) or the retention of the antibody-polymerase complex (where an antibody-polymerase complex if provided); (2) bringing the solution to a denaturation temperature (e.g., about 95° C.) for a second predetermined amount of time (e.g., 60 seconds), which results in denaturation of the antibody and template DNA; (3) bringing the solution to the denaturation temperature (e.g., about 95° C.) for a third predetermined amount of time (e.g., 15 seconds); (4) bringing the solution to an annealing temperature (e.g., about 60° C.) for a fourth predetermined amount of time (e.g., 15 seconds); (5) bringing the solution to an extension temperature (e.g., about 72° C.) for a fifth predetermined amount of time (e.g., 30 seconds); and (6) bringing the solution to an extension temperature (e.g., about 72° C.) for a sixth predetermined amount of time (e.g., 60 seconds), to extend all amplicons produced. In some embodiments, the method further comprises repeating a plurality (e.g., 1-12, 6-18, 12-24, 18-30, 24-36, or 30-40) of times: (a) bringing the solution to the denaturation temperature for the third predetermined amount of time; (b) bringing the solution to the annealing temperature for the fourth predetermined amount of time; and (c) bringing the solution to the extension temperature for the fifth predetermined amount of time.

Kits

In some embodiments, this disclosure provides kits comprising: (a) an antibody of the present disclosure; (b) a dNTP mixture; (c) a reaction buffer; and (d) a Taq polymerase. The reaction buffer is a solution that provides a sufficient chemical environment for a nucleic acid amplification reaction to occur. The reaction buffer may contain: buffering agents (e.g., Tris) to maintain a stable pH, salts or ions (e.g., $K^+$, $Na^+$, or $Mg_2^+$) as cofactors for the polymerase, detergents (e.g., Tween-20 or Triton X-100) to reduce nonspecific DNA binding to reaction tubes or surfaces, stabilizers (e.g., bovine serum albumin (BSA) or gelatin) to minimize PCR inhibition caused by impurities in the DNA template or reaction components, dyes (e.g., bromophenol blue or xylene cyanol FF) for visualizing sample loading during electrophoresis, and/or PCR enhancers (e.g., betaine or DMSO) which can help reduce secondary structures or improve the amplification of challenging templates. In some embodiments, the antibody, the dNTP mixture, the reaction buffer, and the Taq polymerase are provided as a single solution. In some embodiments, the Taq polymerase is a wild-type Taq polymerase. In some embodiments, the Taq polymerase is a variant Taq polymerase.

In some embodiments, this disclosure provides a kit comprising: (a) an antibody-polymerase complex of the present disclosure; (b) a dNTP mixture; and (c) a reaction buffer. In some embodiments, the antibody-polymerase complex, the dNTP mixture, and the reaction buffer are provided as a single solution.

EXAMPLES

Example 1. Hot-Start Antibody Production, Identification, and Characterization New Zealand rabbits were immunized with aCat173 Taq DNA polymerase. Following immunization, total IgG were isolated and aCat173 Taq DNA polymerase-specific IgG was subsequently produced in Chinese Hamster Ovary (CHO) cells initially by transient expression, followed by the creation of a stable expression cell line. Twenty-nine unique monoclonal antibodies were isolated from CHO cell lysates and identified as having specific activity against aCat173 Taq DNA polymerase by ELISA. The monoclonal antibodies were purified from the lysate using anion exchange magnetic beads.

Figure 2:
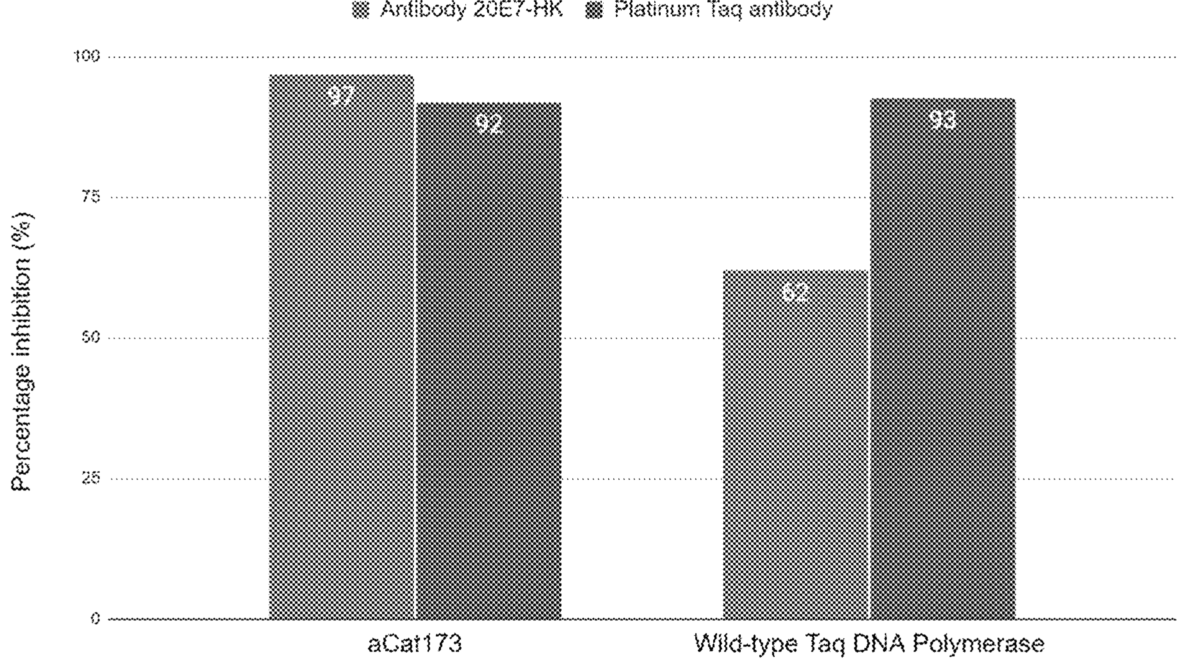
FIG. 2 shows percentage inhibition of a variant Taq DNA polymerase (aCat173) and a wild-type Taq DNA polymerase by antibody 20E7-HK and Platinum® Taq antibody at a 1:0.8 molar ratio (antibody:Taq DNA polymerase).

Antibody activity was evaluated by performing a polymerase inhibiting antibody function assay (PIAFA). The PIAFA is used to assess polymerization activity in the presence of function or heat-inactivated antibody. The malachite green-based polymerization assay was first used to test antibody blocking activity on wildtype and aCat173 Taq DNA polymerase to identify a candidate antibody. An excess of the twenty-nine antibody clones and Platinum® Taq Monoclonal Antibody (Invitrogen, USA) were separately combined with a Taq DNA polymerase. The percentage inhibition was then determined using the malachite green-based assay and quantified by dividing the polymerization activity in the presence of the active antibody by the polymerization activity in the sample where the antibody was heat-inactivated. Of the antibody clones tested, antibody 20E7-HK was identified as a clear candidate, showing high specificity for inhibiting a variant aCat173 Taq DNA polymerase compared to a Platinum® Taq antibody (FIG. 1). The activity of antibody 20E7-HK was further confirmed using the EvaEZ Fluorometric Polymerase Activity Assay Kit and a 1:0.8 molar ratio of antibody (20E7-HK or Platinum® Taq antibody):Taq DNA polymerase. These results confirm that antibody 20E7-HK exhibits more specific inhibiting activity against a variant Taq DNA polymerase than a Platinum® Taq antibody (FIG. 2). Additionally, results showed that the 20E7-HK antibody inhibited the variant aCat173 Taq polymerase much better than it inhibited wildtype Taq polymerase.

Figure 3:
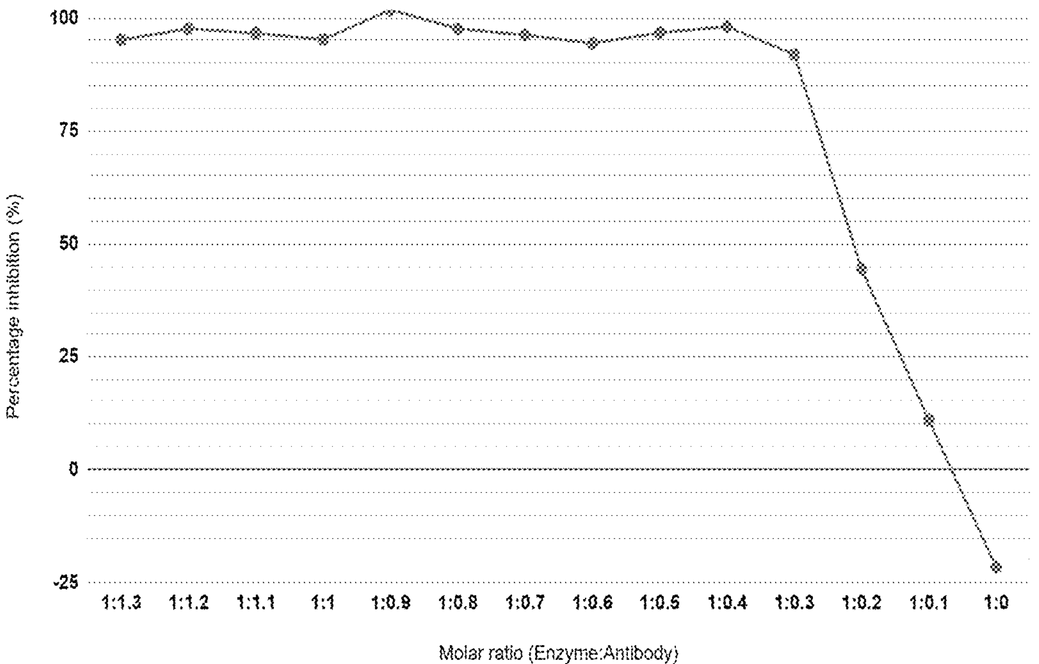
FIG. 3 shows percentage inhibition of a variant Taq DNA polymerase (aCat173) by antibody 20E7-HK at different molar ratios.

To determine the molar ratio of antibody to variant aCat173 Taq DNA polymerase needed to inhibit the polymerase, different molar ratios of antibody 20E7-HK:Taq DNA polymerase were assessed using the EvaEZ Fluorometric Polymerase Activity Assay Kit (Biotium, USA). Molar ratios (polymerase:antibody) of 1:0, 1:0.1, 1:0.2, 1:0.3, 1:0.4, 1:0.5, 1:0.6, 1:0.7, 1:0.8, 1:0.9, 1:1, 1:1.1, 1:1.2, and 1:1.3 were evaluated (FIG. 3). Results from the EvaEZ Fluorometric Polymerase Activity assay showed that antibody 20E7-HK only started to lose efficacy below a molar ratio of 1:0.4 polymerase:antibody). These results indicate that antibody 20E7-HK is an effective hot-start variant aCat173 Taq DNA polymerase antibody.

Methods

Malachite green-based polymerization assay: A reaction mixture containing 0.4 μg/μL activated calf thymus DNA (Sigma-Aldrich), 0.2 mM dNTPs, 8 mM MgCl2, 20 mM Tris-HCl pH 8.3, 40 mM KCl and 0.004% Tween-20 was prepared. Each sample was split into two, and one half was heat treated at 90° C. for 2 minutes to denature and produce heat-inactivated antibodies. The heat-treated (e.g., heat-inactivated) and non-heat-treated (e.g., functional) antibodies were then added to the reaction mixture such that each reaction contained 1 ng of Taq DNA polymerase. Where an excess of antibody was used, antibody-Taq polymerase complexes were prepared with 4 times molar excess of antibody. The reaction mixtures were incubated at 37° C. for 16 hours. The reaction mixtures were then incubated with an excess of inorganic pyrophosphatase to convert the pyrophosphate byproduct to monophosphate. The monophosphate was quantified by color reaction using the Malachite Green Phosphate Assay Kit (Sigma-Aldrich). The absorbance was measured at 600-660 nm using a spectrophotometer. The percentage inhibition was calculated by dividing the non-heated sample's absorbance by the heated sample's absorbance, converting to percentage by multiplying with 100 and subtracting the result from the theoretical 100%.

EvaEZ fluorometric polymerase activity assay (Biotium, USA): A reaction mixture containing 1× EvaEz master mix and antibody-Taq DNA polymerase complexes (at different molar ratios and as described above, heated and non-heated) such that the Taq DNA polymerase concentration was 0.75 ng/μL, was incubated at 37° C. for 1 hour. A real-time qPCR instrument was used to measure the fluorescence in the FAM channel (emission 520 nm). The initial rate of fluorescence change (fluorescence unit/second) resulting from the polymerase activity was obtained by taking the slope of the fluorescence change during the initial velocity of the enzymatic reaction. The percentage inhibition was calculated as described above by using the slopes of the non-heated and heated samples.

What is claimed is:

1. An antibody that binds to a Taq polymerase, wherein the antibody comprises:

(i) a heavy chain comprising a heavy chain variable region (VH); and (ii) a light chain comprising a light chain variable region (VL);

wherein the VH comprises a heavy chain complementarity determining region 1 (CDR-H1) comprising an amino acid sequence as set forth in SEQ ID NO: 3, a heavy chain complementarity determining region 2 (CDR-H2) comprising an amino acid sequence as set forth in SEQ ID NO: 4, a heavy chain complementarity determining region 3 (CDR-H3) comprising an amino acid sequence as set forth in SEQ ID NO: 5; and wherein the VL comprises a light chain complementarity determining region 1 (CDR-L1) comprising an amino acid sequence as set forth in SEQ ID NO: 6, a light chain complementarity determining region 2 (CDR-L2) comprising an amino acid sequence as set forth in SEQ ID NO: 7, and a light chain complementarity determining region 3 (CDR-L3) comprising an amino acid sequence as set forth in SEQ ID NO: 8.

2. The antibody of claim 1, wherein the VH comprises an amino acid sequence as set forth in SEQ ID NO: 9, and the VL comprises an amino acid sequence as set forth in SEQ ID NO: 10.

3. The antibody of claim 1, wherein the heavy chain further comprises a heavy chain constant region (CH) and/or wherein the light chain further comprises a light chain constant region (CL).

4. The antibody of claim 1, wherein the heavy chain comprises an amino acid sequence as set forth in SEQ ID NO: 1, and wherein the light chain comprises an amino acid sequence as set forth in SEQ ID NO: 2.

5. An antibody-polymerase complex, wherein the complex comprises:

(i) the antibody of claim 1; and (ii) a Taq polymerase.

6. A kit comprising:

(a) the antibody of claim 1;

(b) a dNTP mixture;

(c) a reaction buffer; and (d) a Taq polymerase.

7. The kit of claim 6, wherein the antibody, the dNTP mixture, the reaction buffer, and the Taq polymerase are provided as a single solution.

8. A kit comprising:

(a) the antibody-polymerase complex of claim 5;

(b) a dNTP mixture; and (c) a reaction buffer.

9. The kit of claim 8, wherein the antibody-polymerase complex, the dNTP mixture, and the reaction buffer are provided as a single solution.

10. A nucleic acid sequence encoding the antibody of claim 1.

11. An expression vector comprising the nucleic acid sequence of claim 10.

12. A cell comprising the nucleic acid sequence of claim 10.

13. A method of amplifying a nucleic acid template, the method comprising:

combining, in a solution for amplifying the nucleic acid template:

(a) the antibody of claim 1 and a Taq polymerase (b) a dNTP mixture, (c) a target nucleic acid template, and (d) an oligonucleotide primer comprising a polynucleotide that is complementary to the nucleic acid template.

14. The method of claim 13, wherein the Taq polymerase is a wild-type Taq polymerase or wherein the Taq polymerase is a variant Taq polymerase.

15. The method of claim 13, wherein combining occurs at a first temperature, optionally wherein the first temperature is below 30° C.

16. The method of claim 15, further comprising bringing the solution to a denaturation temperature, optionally wherein the denaturation temperature is at least 80° C.

17. The method of claim 16, further comprising bringing the solution to an annealing temperature, optionally wherein the method further comprises bringing the solution to an extension temperature.

18. The method of claim 13, wherein amplification is carried out by PCR, qPCR, digital PCR, droplet digital PCR, linear amplification, or multiplex PCR.

* * * * *

SEQUENCE LISTING

```
Sequence total quantity: 12
SEQ ID NO: 1            moltype = AA  length = 465
FEATURE                 Location/Qualifiers
source                  1..465
                        mol_type = protein
                        organism = synthetic construct
SEQUENCE: 1
MGWSCIILFL VATATGVHSQ SVEESGGRLV TPGTPLTLTC TASGFSLSNY EMNWVRQAPG  60
KGLEWIGIIY GGSANIWYAS WVKGRVTISK TSTTVDLKIT SPTTEDTATY FCARGVYVIY  120
GGDDGSSRLD LWGQGTLVTV SSGQPKAPSV FPLAPCCGDT PSSTVTLGCL VKGYLPEPVT  180
VTWNSGTLTN GVRTFPSVRQ SSGLYSLSSV VSVTSSSQPV TCNVAHPATN TKVDKTVAPS  240
TCSKPTCPPP ELLGGPSVFI FPPKPKDTLM ISRTPEVTCV VVDVSQDDPE VQFTWYINNE  300
QVRTARPPLR EQQFNSTIRV VSTLPIAHQD WLRGKEFKCK VHNKALPAPI EKTISKARGQ  360
PLEPKVYTMG PPREELSSRS VSLTCMINGF YPSDISVEWE KNGKAEDNYK TTPAVLDSDG  420
SYFLYSKLSV PTSEWQRGDV FTCSVMHEAL HNHYTQKSIS RSPGK                465

SEQ ID NO: 2            moltype = AA  length = 234
FEATURE                 Location/Qualifiers
source                  1..234
                        mol_type = protein
                        organism = synthetic construct
SEQUENCE: 2
MGWSCIILFL VATATGVHSA AVLTQTPSPV SAAVGGTVTI NCQSSQTVYN DNDLAWYQQK  60
PGQPPKLLIY AASYLASGVP SRFSGSGSGFGT QFTLTISGVQ CDDAATYYCL GGYDDATDNV  120
FGGGTEVVVK GDPVAPTVLI FPPAADQVAT GTVTIVCVAN KYFPDVTVTW EVDGTTQTTG  180
IENSKTPQNS ADCTYNLSST LTLTSTQYNS HKEYTCKVTQ GTTSVVQSFN RGDC      234

SEQ ID NO: 3            moltype = AA  length = 5
FEATURE                 Location/Qualifiers
source                  1..5
                        mol_type = protein
                        organism = synthetic construct
SEQUENCE: 3
NYEMN                                                            5

SEQ ID NO: 4            moltype = AA  length = 17
FEATURE                 Location/Qualifiers
source                  1..17
                        mol_type = protein
                        organism = synthetic construct
SEQUENCE: 4
IIYGGSANIW YASWVKG                                               17

SEQ ID NO: 5            moltype = AA  length = 17
FEATURE                 Location/Qualifiers
source                  1..17
                        mol_type = protein
                        organism = synthetic construct
SEQUENCE: 5
GVYVIYGGDD GSSRLDL                                               17

SEQ ID NO: 6            moltype = AA  length = 13
FEATURE                 Location/Qualifiers
source                  1..13
                        mol_type = protein
                        organism = synthetic construct
SEQUENCE: 6
```

```
QSSQTVYNDN DLA                                                  13

SEQ ID NO: 7            moltype = AA  length = 7
FEATURE                 Location/Qualifiers
source                  1..7
                        mol_type = protein
                        organism = synthetic construct
SEQUENCE: 7
AASYLAS                                                         7

SEQ ID NO: 8            moltype = AA  length = 11
FEATURE                 Location/Qualifiers
source                  1..11
                        mol_type = protein
                        organism = synthetic construct
SEQUENCE: 8
LGGYDDATDN V                                                    11

SEQ ID NO: 9            moltype = AA  length = 142
FEATURE                 Location/Qualifiers
source                  1..142
                        mol_type = protein
                        organism = synthetic construct
SEQUENCE: 9
MGWSCIILFL VATATGVHSQ SVEESGGRLV TPGTPLTLTC TASGFSLSNY EMNWVRQAPG  60
KGLEWIGIIY GGSANIWYAS WVKGRVTISK TSTTVDLKIT SPTTEDTATY FCARGVYVIY  120
GGDDGSSRLD LWGQGTLVTV SS                                        142

SEQ ID NO: 10           moltype = AA  length = 130
FEATURE                 Location/Qualifiers
source                  1..130
                        mol_type = protein
                        organism = synthetic construct
SEQUENCE: 10
MGWSCIILFL VATATGVHSA AVLTQTPSPV SAAVGGTVTI NCQSSQTVYN DNDLAWYQQK  60
PGQPPKLLIY AASYLASGVP SRFSGSGFGT QFTLTISGVQ CDDAATYYCL GGYDDATDNV  120
FGGGTEVVVK                                                      130

SEQ ID NO: 11           moltype = DNA  length = 3026
FEATURE                 Location/Qualifiers
source                  1..3026
                        mol_type = other DNA
                        organism = synthetic construct
SEQUENCE: 11
atgaggggga tgctgcccct ctttgagccc aagggccggg tcctcctggt ggacggccac  60
cacctggcct accgcacctt ccacgccctg aagggcctca ccaccagccg gggggagccg  120
gtgcaggcgg tctacggctt cgccaagagc ctcctcaagg ccctcaagga ggacggggac  180
gcggtgatcg tggtctttga cgccaaggcc ccctccttcc gccacgaggc ctacgggggg  240
tacaaggcgg gccgggcccc cacgccggag gactttcccc ggcaactcgc cctcatcaag  300
gagctggtgg acctcctggg gctggcgcgc ctcgaggtcc cgggctacga ggcggacgac  360
gtcctggcca gcctggccaa gaaggcggaa aaggagggct acgaggtccg catcctcacc  420
gccgacaaag acctttacca gctcctttcc gaccgcatcc acgccctcca ccccgagggg  480
tacctcatca ccccggcctg gctttgggaa aagtacggcc tgaggcccga ccagtgggcc  540
gactaccggg ccctgaccgg ggacgagtcc gacaaccttc ccggggtcaa gggcatcggg  600
gagaagacgg cgaggaagct tctggaggag tgggggagcc tggaagccct cctcaagaac  660
ctggaccggc tgaagcccgc catccgggag aagatcctgg cccacatgga cgatctgaag  720
ctctcctggg acctggccaa ggtgcgcacc gacctgcccc tggaggtgga cttcgccaaa  780
aggcgggagc ccgaccggga gaggcttagg gcctttctgg agaggcttga gtttggcagc  840
ctcctccacg agttcggcct tctggaaagc cccaaggccc tggaggaggc cccctggccc  900
ccgccggaag gggccttcgt gggctttgtg ctttcccgca aggagcccat gtgggccgat  960
cttctggccc tggccgccgc caggggggc cgggtccacc gggcccccga gccttataaa  1020
gccctcaggg acctgaagga ggcgcggggg cttctcgcca aagacctgag cgttctggcc  1080
ctgagggaag gccttggcct cccgcccggc gacgacccca tgctcctcgc ctacctcctg  1140
gacccttcca acaccacccc cgagggggtg gcccggcgct acggcgggga gtggacggag  1200
gaggcggggg agcgggccgc cctttccgag aggctcttcg ccaacctgtg gggaggctt  1260
gagggggagg agaggctcct ttggctttac cgggaggtgg agaggcccct ttccgctgtc  1320
ctggcccaca tggaggccac gggggtgcgc ctggacgtgg cctatctcag ggccttgtcc  1380
ctggaggtgg ccgaggagat cgcccgcctc gaggccgagg tcttccgcct ggccggccac  1440
cccttcaacc tcaactcccg ggaccagctg gaaagggtcc tctttgacga gctagggctt  1500
cccgccatcg gcaagacgga gaagaccggc aagcgctcca ccagcgccgc cgtcctggag  1560
gccctccgcg aggcccaccc catcgtggag aagatcctgc agtaccggga gctcaccaag  1620
ctgaagagca cctacattga ccccttgccg gacctcatcc accccaggac gggccgcctc  1680
cacacccgct tcaaccagac ggccacggcc acgggcaggc taagtagctc cgatcccaac  1740
ctccagaaca tccccgtccg caccccgctt gggcagagga tccgccgggc cttcatcgcc  1800
gaggaggggt ggctattggt ggccctggac tatagccaga tagagctcag ggtgctggcc  1860
cacctctccg gcgacgagaa cctgatccgg gtcttccagg aggggcggga catccacacg  1920
gagaccgcca gctggatgtt cggcgtcccc cgggaggccg tggacccct gatgcgccgg  1980
gcggccaaga ccatcaactt cggggtcctc tacggcatgt cggcccaccg cctctcccag  2040
gagctagcca tcccttacga ggaggcccag gccttcattg agcgctactt tcagagcttc  2100
```

-continued

```
cccaaggtgc gggcctggat tgagaagacc ctggaggagg gcaggaggcg ggggtacgtg  2160
gagaccctct tcggccgccg ccgctacgtg ccagacctag aggcccgggt gaagagcgtg  2220
cgggaggcgg ccgagcgcat ggccttcaac atgcccgtcc agggcaccgc cgccgacctc  2280
atgaagctgg ctatggtgaa gctcttcccc aggctggagg aaatgggggc caggatgctc  2340
cttcaggtcc acgacgagct ggtcctcgag gccccaaaag agagggcgga ggccgtggcc  2400
cggctggcca aggaggtcat ggagggggtg tatcccctgg ccgtgcccct ggaggtggag  2460
gtggggatag gggaggactg gctctccgcc aaggagtgat accaccccat gctggcccaa  2520
gccagcatgg gggccccggc aaaaggtttc tggggaagtt accaggcatg gtgggccgaa  2580
ggaaacagga aacaagggta tgagggtttt ttgccctaaa gaaaggccag gggtcctcc   2640
cgaaggaagg cttccagggg gatacccct  gggcccagga gtagcccctt tcctccaaag  2700
gcctgggtga aggcttttag ccctttggtc ctttgggaag gggcgctttt gacctccaaa  2760
gccagaaggc gccttccctt cttcaagacg aagtcaacct cctggtccct ttcccgccag  2820
tagtacacct caaagccccc gtgggggccg tgggccagaa ggtgggcgcc cacggcggtt  2880
tccacgagcc gccccatgag ggcggcgtcc gcccacacct cctttgggga aagccccaag  2940
accgccgtga tgagccccgt attaagggcc aggagcttgg ggctcgaggc gcggcgccgg  3000
aagggctcgg cggcgtactt ctgcag                                        3026

SEQ ID NO: 12          moltype = AA  length = 832
FEATURE                Location/Qualifiers
source                 1..832
                       mol_type = protein
                       organism = synthetic construct
SEQUENCE: 12
MRGMLPLFEP KGRVLLVDGH HLAYRTFHAL KGLTTSRGEP VQAVYGFAKS LLKALKEDGD  60
AVIVVFDAKA PSFRHEAYGG YKAGRAPTPE DFPRQLALIK ELVDLLGLAR LEVPGYEADD  120
VLASLAKKAE KEGYEVRILT ADKDLYQLLS DRIHALHPEG YLITPAWLWE KYGLRPDQWA  180
DYRALTGDES DNLPGVKGIG EKTARKLLEE WGSLEALLKN LDRLKPAIRE KILAHMDDLK  240
LSWDLAKVRT DLPLEVDFAK RREPDRERLR AFLERLEFGS LLHEFGLLES PKALEEAPWP  300
PPEGAFVGFV LSRKEPMWAD LLALAAARGG RVHRAPEPYK ALRDLKEARG LLAKDLSVLA  360
LREGLGLPPG DDPMLLAYLL DPSNTTPEGV ARRYGGEWTE EAGERAALSE RLFANLWGRL  420
EGEERLLWLY REVERPLSAV LAHMEATGVR LDVAYLRALS LEVAEEIARL EAEVFRLAGH  480
PFNLNSRDQL ERVLFDELGL PAIGKTEKTG KRSTSAAVLE ALREAHPIVE KILQYRELTK  540
LKSTYIDPLP DLIHPRTGRL HTRFNQTATA TGRLSSSDPN LQNIPVRTPL GQRIRRAFIA  600
EEGWLLVALD YSQIELRVLA HLSGDENLIR VFQEGRDIHT ETASWMFGVP REAVDPLMRR  660
AAKTINFGVL YGMSAHRLSQ ELAIPYEEAQ AFIERYFQSF PKVRAWIEKT LEEGRRRGYV  720
ETLFGRRRYV PDLEARVKSV REAAERMAFN MPVQGTAADL MKLAMVKLFP RLEEMGARML  780
LQVHDELVLE APKERAEAVA RLAKEVMEGV YPLAVPLEVE VGIGEDWLSA KE          832
```